United States Patent
Bartsch et al.

(10) Patent No.: US 7,361,778 B2
(45) Date of Patent: Apr. 22, 2008

(54) METHOD FOR THE ISOMERIZATION OF CIS-2-PENTENENITRILE TO FORM TRANS-3-PENTENENITRILE

(75) Inventors: Michael Bartsch, Neustadt (DE);
Robert Baumann, Mannheim (DE);
Gerd Haderlein, Grünstadt (DE);
Miquel Angel Flores, Aranjuez (ES);
Tim Jungkamp, Kapellen (BE);
Hermann Luyken, Ludwigshafen (DE);
Jens Scheidel, Hirschberg (DE);
Wolfgang Siegel, Limburgerhof (DE);
Dagmar Pascale Kunsmann-Keitel, Limburgerhof (DE)

(73) Assignee: BASF Aktiengesellschaft (DE)

( * ) Notice: Subject to any disclaimer, the term of this patent is extended or adjusted under 35 U.S.C. 154(b) by 229 days.

(21) Appl. No.: 10/553,916

(22) PCT Filed: Apr. 16, 2004

(86) PCT No.: PCT/EP2004/004040

§ 371 (c)(1),
(2), (4) Date: Oct. 20, 2005

(87) PCT Pub. No.: WO2004/094364

PCT Pub. Date: Nov. 4, 2004

(65) Prior Publication Data

US 2006/0194979 A1    Aug. 31, 2006

(30) Foreign Application Priority Data

Apr. 22, 2003   (DE) ................. 103 23 803

(51) Int. Cl.
*C07C 253/30*    (2006.01)
(52) U.S. Cl. ....................... 558/462
(58) Field of Classification Search ............ 558/462
See application file for complete search history.

(56) References Cited

U.S. PATENT DOCUMENTS 3,526,654 A   9/1970   Hildebrand
3,852,325 A   12/1974  King

*Primary Examiner*—Kamal A. Saeed
(74) *Attorney, Agent, or Firm*—Connolly Bove Lodge & Hutz, LLP

(57) ABSTRACT

A process for isomerizing cis-2-pentenenitrile to trans-3-pentenenitrile in the presence of aluminum oxide as a catalyst, wherein the aluminum oxide has a BET surface area of at least 50 $m^2/g$.

12 Claims, No Drawings

METHOD FOR THE ISOMERIZATION OF CIS-2-PENTENENITRILE TO FORM TRANS-3-PENTENENITRILE

RELATED APPLICATIONS

This application is a national stage application (under 35 U.S.C. 371) of PCT/EP2004/004040 filed Apr. 16, 2004 which claims benefit to German application 103 23 803.4 filed Apr. 22, 2003.

The present invention relates to a process for isomerizing cis-2-pentenenitrile to trans-3-pentenenitrile in the presence of aluminum oxide as a catalyst, wherein the aluminum oxide has a BET surface area of at least 50 $m^2/g$.

The hydrocyanation of 3-pentenenitrile to adiponitrile, which constitutes an important starting compound for preparing polyamides, in the presence of an Ni(0)-containing catalyst is known to result in the by-production of cis-2-pentenenitrile. This cis-2-pentenenitrile typically cannot, unlike 3-pentenenitrile such as trans-3-pentenenitrile, be hydrocyanated to adiponitrile in the presence of one of the Ni(0)-containing catalysts mentioned, and thus reduces the yield in the adiponitrile synthesis.

It is therefore desirable to isomerize the cis-2-pentenenitrile to trans-3-pentenenitrile, in order then to be able to recycle it back into the adiponitrile synthesis.

U.S. Pat. No. 3,526,654 discloses the isomerization of cis-2-pentenenitrile to trans-3-pentenenitrile in the presence of silicon dioxide, aluminum oxide or sodium calcium silicate catalysts which may be present in various modifications, in the liquid or gas phase at temperatures in the range from 25° C. to 500° C. Example 3 describes the isomerization mentioned over aluminum oxide at room temperature in the liquid phase, and a conversion of 40% was observed after 6 months. However, this reaction time is uneconomic for an industrial process.

Typically, the reaction rate can be increased by raising the reaction temperature. This measure is not suitable for the purpose in the present isomerization of cis-2-pentenenitrile to trans-3-pentenenitrile, since, in the case of pentenenitriles, an increase in the reaction temperature within the temperature range disclosed in U.S. Pat. No. 3,526,654 is known to lead to the formation of an industrially unacceptably high amount of oligomers and polymers.

It is an object of the present invention to provide a process which enables cis-2-pentenenitrile to be isomerized to trans-3-pentenenitrile in a technically simple and economic manner.

We have found that this object is achieved by the process defined at the outset.

The cis-2-pentenenitrile used in the process according to the invention may be obtained by processes known per se, for example by the process already cited at the outset as a by-product in the hydrocyanation of 3-pentenenitrile such as trans-3-pentenenitrile or cis-3-pentenenitrile or mixtures thereof, or mixtures comprising such 3-pentenenitrile, to adiponitrile.

In an advantageous embodiment, the process according to the invention can be integrated in such a hydrocyanation process for preparing adiponitrile.

In a particularly advantageous embodiment, such an integration can be effected by a) hydrocyanating 3-pentenenitrile or a mixture comprising 3-pentenenitrile in the presence of an Ni(0)-containing catalyst by processes known per se to give adiponitrile, while obtaining cis-2-pentenenitrile as a by-product, b) removing cis-2-pentenenitrile from the product mixture, for example by distillation, c) isomerizing cis-2-pentenenitrile from step b) by a process according to the invention to obtain a product stream comprising trans-3-pentenenitrile, and in addition possibly trans-2-pentenenitrile or cis-3-pentenenitrile, d) removing any cis-2-pentenenitrile present in the product stream obtained in step c), for example by distillation, and recycling it into step c) to obtain a residue stream, e) recycling the residue stream obtained in step d) in step a).

The Ni(0)-containing catalyst used in step a) may preferably be one which, in addition to Ni(0), also has a polydentate ligand, in particular a chelate ligand, which has a plurality of, such as two or three, trivalent phosphorus atoms which are capable of bonding to the said Ni(0) and may each independently be present as phosphine, phosphinite, phosphonite or phosphite. The catalyst should particularly advantageously also comprise a Lewis acid. Such catalyst systems are known per se.

According to the invention, the isomerization is carried out in the presence of aluminum oxide as a catalyst, and the aluminum oxide has a BET surface area of at least 50 $m^2/g$, preferably at least 70 $m^2/g$, in particular at least 100 $m^2/g$.

The aluminum oxide should advantageously have a BET surface area of at most 400 $m^2/g$, preferably at most 350 $m^2/g$, in particular at most 300 $m^2/g$.

In the context of the present invention, the BET surface area refers to the specific surface area determined by measuring the physisorbed amount of gas by the method described in Brunauer, Emmett, Teller, J. Am. Chem. Soc. 60 (1938) page 309.

The aluminum oxide may be present in pure form.

It is possible to use aluminum oxide which contains further compounds, such as rare earth oxides, for example cerium oxide, praseodymium oxide, silicon dioxide, titanium dioxide, iron oxide, alkali metal oxides, alkaline earth metal oxides or mixtures thereof. Such compounds may be present in amounts of from at least 10 ppm by weight up to at most 10% by weight, based on the sum of aluminum oxide and such compounds.

In addition to the oxide anion, further anions such as hydroxide anions may also be present.

The isomerization of cis-2-pentenenitrile to trans-3-pentenenitrile may advantageously be carried out up to partial conversion to obtain a mixture which comprises cis-2-pentenenitrile and trans-3-pentenenitrile. Typically, the product mixture may comprise further isomeric pentenenitriles such as trans-2-pentenenitrile, cis-3-pentenenitrile, 4-pentenenitrile, 2-methyl-2-butenenitrile or mixtures thereof. Unconverted cis-2-pentenenitrile can advantageously be removed from such a mixture, for example by distillation. The residue stream depleted in cis-2-pentenenitrile can preferably be fed to a hydrocyanation.

It is also possible to feed the product mixture obtained in the isomerization to a hydrocyanation without depleting cis-2-pentenenitrile.

Isomerization in the gas phase is possible; in an advantageous embodiment; isomerization in the liquid phase comes into consideration.

The temperature in the isomerization should be at least 50° C., preferably at least 120° C.

The temperature in the isomerization should be at most 250° C., preferably at most 200° C.

The isomerization can be carried out in the presence of a liquid diluent, in particular a liquid diluent which is inert with respect to the pentenenitriles in the isomerization according to the invention, such as a hydrocarbon. Preference is given to isomerizing in the absence of such a liquid diluent.

EXAMPLES 1-5 cis-2-Pentenenitrile (purity 98%) was admixed with 10% by weight, based on cis-2-pentenenitrile, of aluminum oxide powder and heated to reflux under atmospheric pressure for 7 hours (126-144° C., temperature increased in the course of progressing conversion).

The composition was determined by gas chromatography. The results are compiled in table 1.

TABLE 1

| Example | BET SA [$m^2/g$] | c-2PN [% by wt.] | t-2PN [% by wt.] | t-3PN [% by wt.] | c-3PN [% by wt.] | Oligomers [% by wt.] |
|---|---|---|---|---|---|---|
| Comp. Ex. 1 | 31.5 | 94.06 | 0.75 | 2.97 | 0.70 | 0 |
| 1 | 72 | 70.25 | 15.07 | 10.96 | 2.17 | 0 |
| 2 | 106 | 57.24 | 19.95 | 17.89 | 3.23 | 0.17 |
| 3 | 250 | 56.04 | 19.18 | 19.27 | 3.12 | 0.84 |
| 4 | 349 | 39.3 | 34.1 | 18.5 | 5.1 | 1.4 |

BET SA: BET surface area of the particular aluminum oxide
c-2PN: cis-2-pentenenitrile
t-2-PN: trans-2-pentenenitrile
t-3-PN: trans-3-pentenenitrile
c-3-PN: cis-3-pentenenitrile The amounts missing to 100% by weight are residues, for example isomeric nitrites.

It is apparent from comparative example 1 that industrially acceptable isomerization conversions were not achieved using aluminum oxide having a BET surface area of 31.5 [$m^2/g$].

We claim:

1. A process for isomerizing cis-2-pentenenitrile to trans-3-pentenenitrile in the presence of aluminum oxide as a catalyst, wherein the aluminum oxide has a BET surface area of at least 50 $m^2/g$ and the reaction is carried out at a temperature in the range of from 50° C. to 250° C.

2. The process according to claim 1, wherein the aluminum oxide has a BET surface area of at least 70 $m^2/g$.

3. The process according to claim 1, wherein the aluminum oxide has a BET surface area of at most 400 $m^2/g$.

4. The process according to claim 1, wherein the isomerization is carried out in the liquid phase.

5. The process according to claim 1, wherein the reaction is carried out at a temperature of at least 120° C. and at most 200° C.

6. The process according to claim 2, wherein the isomerization is carried out in the liquid phase and the aluminum oxide has a BET surface area of at most 400 $m^2/g$.

7. The process according to claim 6, wherein the reaction is carried out at a temperature of at least 120° C. and at most 200° C.

8. The process according to claim 1, wherein the aluminum oxide has a BET surface area of at least 100 $m^2/g$.

9. The process according to claim 1, wherein the aluminum oxide has a BET surface area of at most 300 $m^2/g$.

10. The process according to claim 7, wherein the aluminum oxide has a BET surface area of at least 100 $m^2/g$ and at most 300 $m^2/g$.

11. The process according to claim 1, wherein the aluminum oxide has a BET surface area of at least 50 $m^2/g$ and at most 400 $m^2/g$.

12. The process according to claim 4, wherein the aluminum oxide has a BET surface area of at least 50 $m^2/g$ and at most 400 $m^2/g$.

* * * * *